Figure 1:
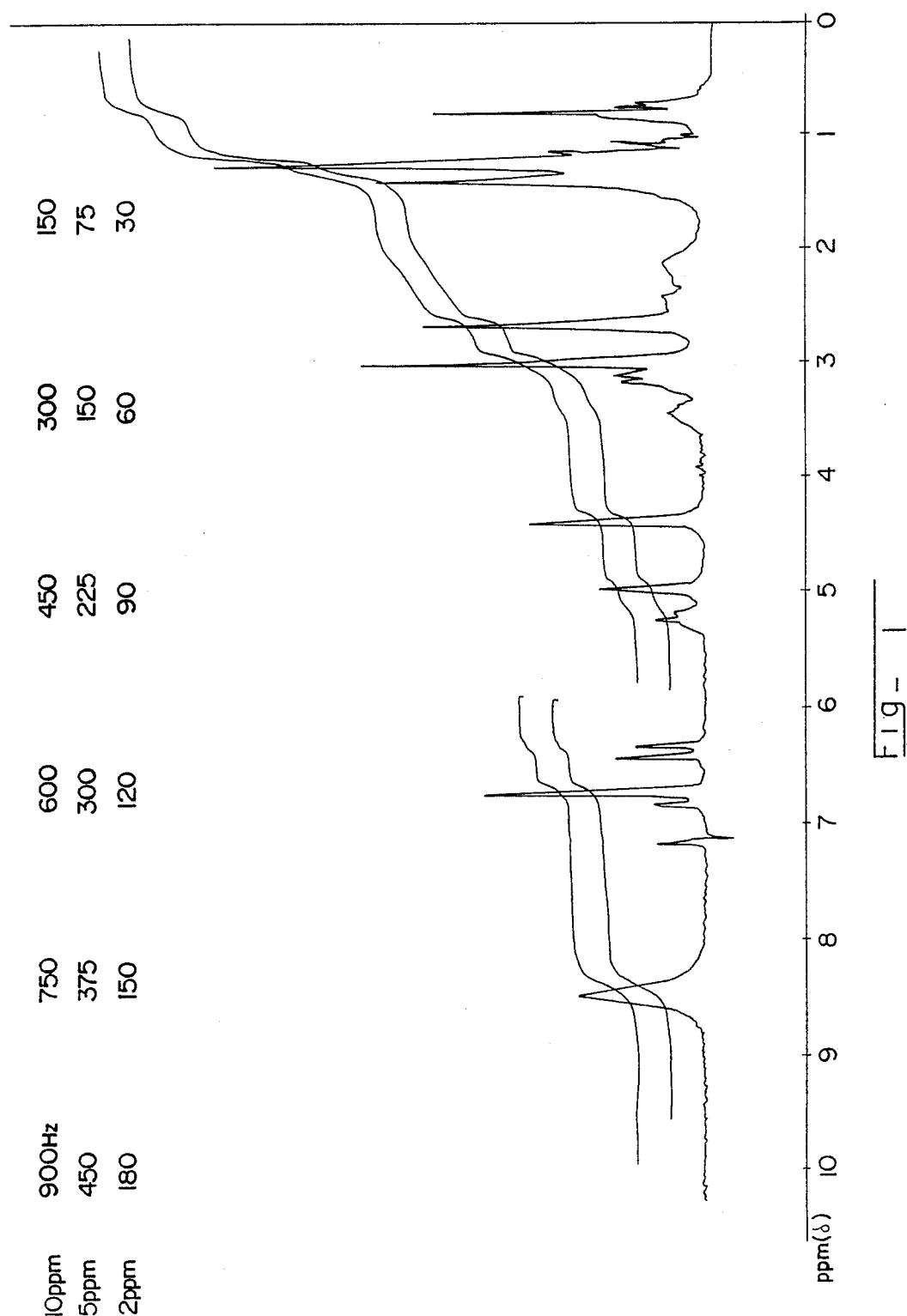

United States Patent [19]

Meroni et al.

[11] Patent Number: 4,978,673
[45] Date of Patent: Dec. 18, 1990

[54] ORGANIC SALTS OF PHYSOSTIGMINE DERIVATIVES

[75] Inventors: Carlo Meroni, Meda; Stefano Maiorana, Milan; Mario Brufani; Massimo Pomponi, both of Rome; Riccardo Bernardi, Artigliano; Pier L. Rugarli, Milan; Pier G. Pagella, Isola S. Antonio, all of Italy

[73] Assignee: Mediolanum Farmaceutici S.r.l. Consiglio Nazionale Delle Ricerch, Italy

[21] Appl. No.: 172,799

[22] Filed: Mar. 28, 1988

[30] Foreign Application Priority Data

Apr. 3, 1987 [IT] Italy .................. 19964 A/87

[51] Int. Cl.$^5$ ............... C07D 487/00; A61K 31/40
[52] U.S. Cl. ................................ 514/411; 548/429
[58] Field of Search .................. 548/429; 514/411

[56] References Cited

FOREIGN PATENT DOCUMENTS 0253372 1/1988 European Pat. Off. ............ 548/429

Primary Examiner—Mary C. Lee
Assistant Examiner—Robert C. Whittenbaugh
Attorney, Agent, or Firm—Arnold, White & Durkee

[57] ABSTRACT

Organic salts of physostigmine derivatives, having the following general formula:

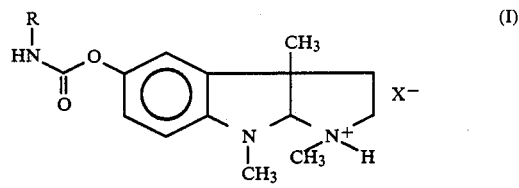

in which R is a linear or branched $C_2$–$C_{12}$ alkyl or a cycloalkyl or an aryl, and $X_-$ is the anion of an organic acid, the process for their preparation and their pharmaceutical use for acetylcholinesterase inhibition purposes.

11 Claims, 3 Drawing Sheets

ORGANIC SALTS OF PHYSOSTIGMINE DERIVATIVES

This invention relates to organic salts of physostigmine derivatives.

More particularly, the invention relates to organic salts of physostigmine derivatives, having the following general formula:

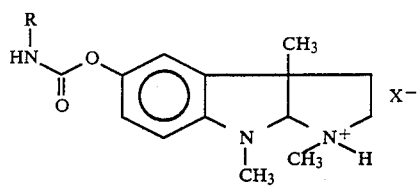
(I)

in which R is a linear or branched $C_2$-$C_{12}$ alkyl or a cycloalkyl or an aryl, and $X-$ is the anion of an organic acid preferably chosen from the group consisting of tartaric acid, maleic acid and citric acid.

The invention also relates to the process for preparing said salts and their use in the preparation of pharmaceutical compounds with acetylcholinesterase inhibition properties.

The anticholinesterase function of physostigmine has been known for some time. It is also well known that a considerable reduction in cerebral acetylcholine concentration occurs in dementia of Alzheimer type, and consequently in treating this pathology it is useful to use medicaments able to increase this concentration.

Although being suitable for this purpose, physostigmine has the drawback of high toxicity, a short duration of action, and peripheral effects which are damaging, particularly to the digestive system.

Physostigmine derivatives of lesser toxicity are also known, such as those described in Italian patent application No. 47780A/84.

However these derivatives have chemical and physical characteristics which make them little suitable for application as they are of waxy solid form or of oily consistency and are insoluble in water and poorly stable towards light and air. Moreover their described production process, based on vacuum synthesis operations, implies technical difficulties with regard to large-scale industrial production and does not allow high-purity products to be obtained, and in addition involves somewhat risky operations in terms of isocyantate toxicity, and low reaction yields.

These drawbacks are obviated by the salts of formula (I) according to the present invention and by the relative production process. In this respect, said salts are highly water-soluble, have high stability towards light and air, have low toxicity and have a long duration of action.

Moreover, their preparation process allows the industrial production of high purity products because of the facility for purifying and crystallising the intermediate derivatives.

The simplification of the method, which does not involve vacuum operations, also results in an increased yield and a reduction in the danger involved in the synthesis.

The process for preparing the salts of formula (I) according to the present invention starts with physostigmine and is implemented in the following stages:

(a) hydrolysing physostigmine in an organic solvent by means of alkalis, followed by inorganic acid treatment to obtain eseroline (II)

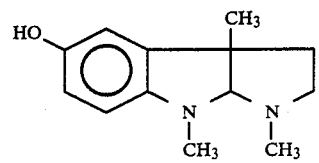
(II)

which is purified by crystallisation;

(b) treating the eseroline in an organic solvent with an isocyanate of formula R—N=C=O in which R is a linear or branched $C_2$-$C_{12}$ alkyl or a cycloalkyl or an aryl, to obtain the corresponding physostigmine derivative (III)

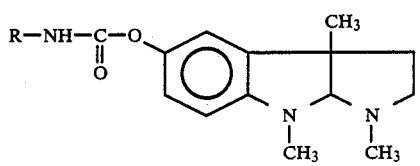
(III)

in which R has the aforesaid meaning;

(c) salifying said physostigmine derivative in an organic solvent with an organic acid to obtain the salt (I).

The physostigmine is hydrolysed in an organic solvent chosen from methanol, ethanol, propanol, dioxane, ethylene glycol and isopropanol, and preferably in absolute ethanol, under a nitrogen atmosphere at ambient temperature, using as reagent an aqueous KOH or NaOH solution, and preferably an aqueous 5–30% w/w NaOH solution.

On termination of the reaction, the hydroalcoholic solution obtained is treated with strong inorganic acids, and preferably with a 1N HCl solution saturated with NaCl.

The product obtained by processing the solution is crystallised from aromatic and aliphatic hydrocarbon mixtures, and preferably from a 1:1 benzene/petroleum ether mixture to obtain eseroline (II) in the pure state.

In treating the eseroline with the isocyanate, the two reagents are dissolved or suspended, each on its own account, in an organic solvent such as ethyl ether, diisopropyl ether, benzene, toluene, xylene or petroleum ether, and preferably in ethyl ether, there then being added to the eseroline solution a trace of an alkaline substance chosen from NaOH, KOH, NaHCO₃, Na₂CO₃, CH₃COONa and Na, and preferably Na, operating under a nitrogen atmosphere at ambient temperature, the diisocyanate solution being added slowly to the eseroline solution until an equimolar ratio of the two reagents is obtained. On termination of the reaction the mixture is washed with water, then the water removed and the physostigmine derivative (III) finally obtained in the dry state by evaporating the reaction solvent.

To salify the physostigmine drivative (III) with the organic acid, said derivative is dissolved in an organic solvent chosen from ethyl ether, ethanol, methanol, isopropanol, diisopropyl ether or their mixtures, and preferably in isopropyl ether or isopropyl alcohol or mixtures thereof, and the organic acid is dissolved in ethanol, methanol, isopropyl alcohol or ethyl ether, and preferably in isopropyl alcohol.

To obtain these solutions, 5-25 ml of solvent per g of the physostigmine derivative and 5-35 ml of solvent per g of organic acid are used.

When the two reagents have completely dissolved, the solutions are mixed under agitation at ambient temperature with the two reagents in equimolar quantities.

The salt precipitates either spontaneously or, if necessary, on adding a suitable solvent, particularly diisopropyl ether, in a volumetric quantity of 3-5 times the volume of solvent used for dissolving the physostigmine derivative.

Precipitation takes place either immediately after mixing or within a period of between 30 minutes and 5 hours.

The product is recovered by filtration and dried at a temperature of between 60° and 90° C. If necessary, the product is purified before or after drying by washing with a suitable apolar or medium polar solvent, in particular ethyl ether. In some cases the product can require grinding.

In this manner the physostigmine organic salts of general formula (I) are obtained with high yield, in high-purity, non-hygroscopic subdivided solid form, with high stability towards air and light.

Evaluation of acetylcholinesterase inhibition activity (enzymatic dosage)

The effect on acetylcholinesterase activity in the brain of male CD/SD rats was evaluated for the salts (I) in which R was $C_7H_{15}$, $C_4H_9$ and $C_9H_{19}$, and X— the tartaric acid anion, and for physostigmine as comparison. The products under examination were administered in the form of an aqueous solution orally by gastric probe to these rats after they had fasted for 18 hours.

A group of rats treated orally with physiological solution acted as control. The rats were sacrificed by decapitation at various times after treatment with the products under examination. Their brains were isolated and acetylcholinesterase activity evaluated thereon by the method described by Ellman et al. (Ellman, G. L., Courtney, K. D., Andres, V., Featherstone, R. M., A New and Rapid Colorimetric Determination of Acetylcholinesterase Activity. Biochem. Pharm., 1961, 7, 88).

The percentage variation in acetylcholinesterase in the brain of rats treated with the products under examination was calculated compared with that in the brain of the rats treated with physiological solution (control group), the results obtained being summarised in Table 1.

TABLE 1

| | | % variation of acetylcholinesterase in the brain of rats | | | | |
|---|---|---|---|---|---|---|
| | | Treatment % variation in brain acetylcholinesterase at given times (in minutes) | | | | |
| Product | mg/kg oral | 15 | M 30 | S.E. 60 | 120 | 240 |
| physostigmine | 1 | 40.50 ±7.51 | 60.27 ±10.35 | 23.37 ±2.94 | 5.23 ±1.40 | |
| (*) | 1 | 25.70 ±2.93 | 33.50 ±2.14 | 26.37 ±3.16 | 24.23 ±3.19 | 15.20 ±3.44 |
| (**) | 1 | 30.20 ±2.71 | 47.27 ±3.73 | 37.43 ±3.43 | 34.60 ±2.82 | 25.80 ±3.45 |
| (***) | 1 | 8.97 | 24.73 | 22.60 | 20.10 | 10.37 |

TABLE 1-continued

| | | % variation of acetylcholinesterase in the brain of rats | | | | |
|---|---|---|---|---|---|---|
| | | Treatment % variation in brain acetylcholinesterase at given times (in minutes) | | | | |
| Product | mg/kg oral | 15 | M 30 | S.E. 60 | 120 | 240 |
| | | ±1.54 | ±6.85 | ±3.87 | ±2.57 | ±1.48 |

(*)salt (I) where R = $C_7H_{15}$ and X— = tartaric acid anion
(**)salt (I) where R = $C_4H_9$ and X— = tartaric acid anion
(***)salt (I) where R = $C_9H_{19}$ and X— = tartaric acid anion The results obtained show that when administered orally to the rat the salts of the invention induce a cerebral acetylcholinesterase inhibiting action of a power comparable to that observed on administering physostigmine but with the advantage that their action is considerably more prolonged.

Finally it must be emphasized that the toxicity of said salts in the rat ($LD_{50}$ equal to 6, 20 and 50 mg/kg/os for the salts **, * and *** respectively) is considerably lower that that of physostigmine.

The following examples are given as non-limiting illustration of the process for preparing the salts (I) according to the present invention.

EXAMPLE 1

Preparation of salt (I) where R=$C_7H_{15}$ and X—=tartaric acid anion (a) Preparation of eseroline (II).

15 g (0.545 moles) of physostigmine and 70 ml of absolute ethanol are fed into a 3-neck 500 ml flask kept under a rigorous nitrogen atmosphere.

When the physostigmine has completely dissolved, 70 ml of a 10% w/w NaOH solution through which nitrogen had previously been bubbled to dispel the air are added.

The hydrolysis reaction is weakly exothermic. The mixture is left under agitation at ambient temperature under a nitrogen flow for a time varying from 1 to 2 hours. About 190 ml of 1N HCl is then added to the hydroalcoholic solution together with a quantity of NaCl such as to saturate the solution.

The reaction mixture is then poured into a separator funnel and about 500 ml of ethyl ether are added.

The mixture is agitated and the aqueous (red) phase is separated.

Washing with water saturated with NaCl is repeated until complete disappearance of colour in the organic phase which is then dried with $Na_2SO_4$ and the ether evaporated under reduced pressure. A pinkish white solid separates and is crystallized from 1:1 benzene/petroleum ether (B.P. 40°-60° C.).

The microcrystalline powdery white product (II) is obtained with a yield of 90%. Product purity is checked by TLC; M.P. 129° C.

(b) Preparation of the physostigmine derivative (III) in which R=$C_7H_{15}$ 10 g (0.0458 moles) of eseroline and 300 ml of ethyl ether are fed into a 1 liter flask fitted with a mechanical stirrer and kept under a nitrogen atmosphere.

A small quantity of Na (about 300 mg) is then added. The presence of the Na prevents the formation of polyalkylation products, so directing the reaction towards the desired product.

When most of the eseroline has dissolved, an equimolar quantity of heptyl isocyanate dissolved in about 50 ml of ethyl ether is added by a dropping funnel. The addition is made slowly so as to maintain a deficiency of isocyanate in relation to the eseroline.

When the addition is complete, the reaction mixture is left under agitation at ambient temperature for a time variable from 5 minutes to half hour.

The progress of the reaction is followed by TLC.

When the eseroline has completely disappeared, the crude reaction mixture is poured into a separator funnel and washed several times with water until the water remains colourless.

After drying the ether solution with $Na_2SO_4$, the ether is evaporated under reduced pressure.

The derivative (III) is obtained with a yield varying from 80 to 90%.

The spectroscopic data (NMR, IR, UV, MASS) and analytical data (elementary analysis) for the obtained product conform to the derivative (III) in which $R = C_7H_{15}$.

Operating in the same manner and reacting the eseroline with the appropriate isocyanates, physostigmine derivatives (III) were prepared in which $R = C_4H_9$, $C_9H_{19}$ and

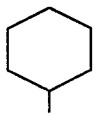

(c) Preparation of the salt (I) in which $R = C_7H_{15}$ and $X^- =$ tartaric acid anion.

10 g (0.0278 moles) of the derivative (III) in which $R = C_7H_{15}$ are dissolved in 80 ml of diisopropyl ether, and 4.17 g (0.0278 moles) of L-tartaric acid are dissolved in 80 ml of isopropyl alcohol.

When the two reagents have completely dissolved, the solutions are mixed under agitation.

After about 30 minutes a microcrystalline powdery white solid begins to precipitate.

When precipitation of the salt is complete, 100 ml of diisopropyl ether are added to the mixture, which is then agitated for about 1 hour.

The salt is then filtered off and dried at 80° C. for about 2 hours.

13 g of product are obtained with a yield of 91%. M.P. 122°–123° C.

| Elementary analysis: | Calculated | Found |
|---|---|---|
| C | 58.9 | 58.82 |
| H | 7.67 | 7.62 |
| N | 8.25 | 8.20 |

Figure 2:
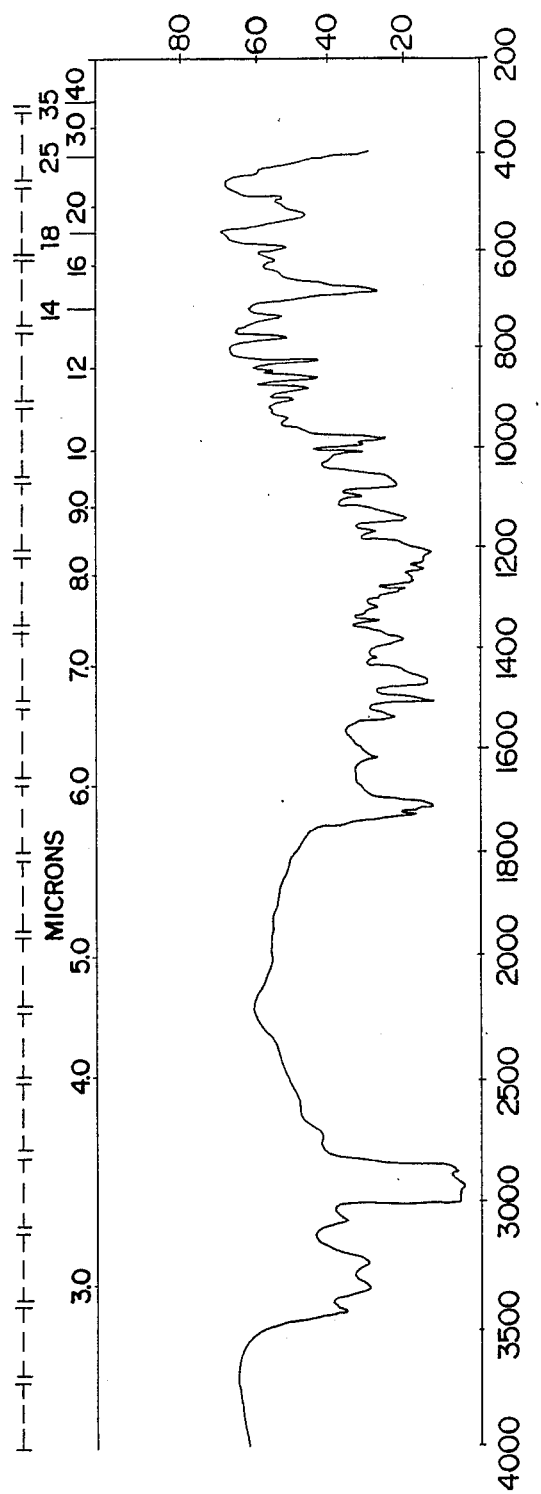
Figure 3:
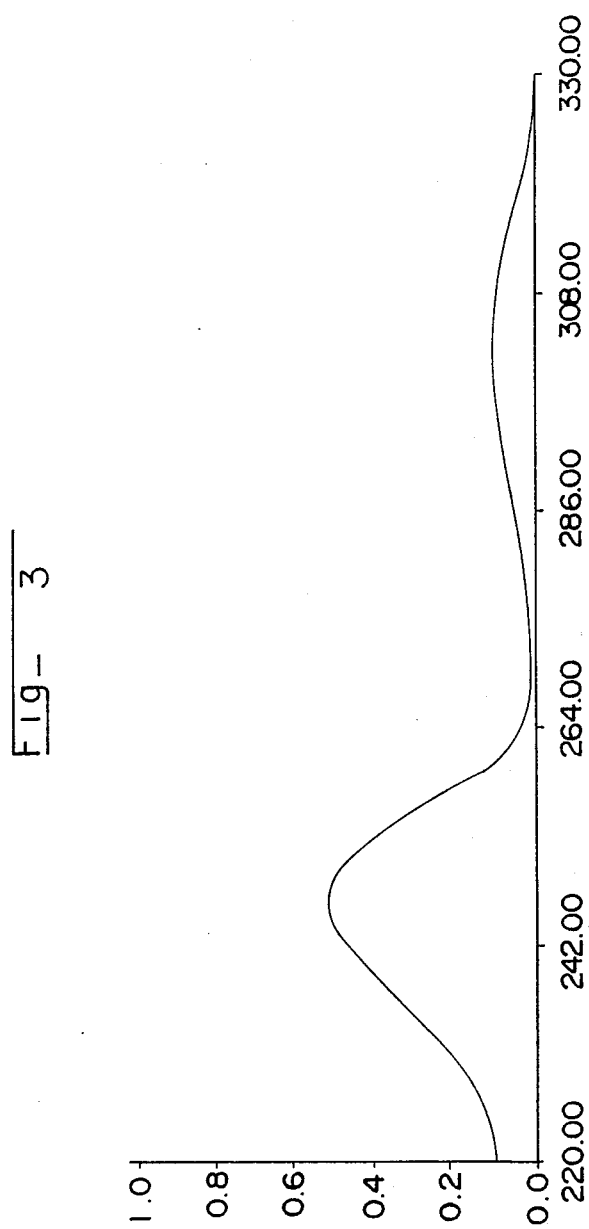

The salt obtained is in the form of a microcrystalline powder with a water solubility of 70%, whereas the corresponding non-salified derivative is an insoluble waxy solid of low melting point. Of this salt we attach by way of example the NMR spectrum in CDCl3 using TMS as reference (FIG. 1), the I.R. spectrum in Nujol (FIG. 2), and the UV spectrum (aqueous solution 20 g/ml) (FIG. 3).

EXAMPLE 2

Preparation of salt (I) where $R = C_4H_9$ and $X^- =$ tartaric acid anion 4.5 g (0.0142 moles) of the derivative (III) in which $R = C_4H_9$ are dissolved in 30 ml of isopropanol, and 2.13 g (0.0142 moles) of L-tartaric acid are dissolved in 20 ml of isopropanol.

When the two reagents have completely dissolved, the solutions are mixed under agitation.

30 ml of isopropyl ether are then added very slowly under strong agitation, the mixture is kept under agitation for 4 hours and a further 100 ml of isopropyl ether are added.

A white flaky precipitate is obtained and filtered off, dried in an oven at 80° C. for 3 hours and then finely ground 5.5 g of product are obtained with a yield of 82%. M.P. 123°–124° C.

| Elementary analysis: | Calculated | Found |
|---|---|---|
| C | 56.53 | 56.45 |
| H | 7.07 | 7.10 |
| N | 8.99 | 8.93 |

EXAMPLE 3

Preparation of salt (I) where $R = C_9H_{19}$ and $X^- =$ tartaric acid anion 8.8 g (0.0227 moles) of the derivative (III) in which $R = C_9H_{19}$ are dissolved in 50 ml of isopropyl ether, and 3.41 g (0.0227 moles) of L-tartaric acid are dissolved in 50 ml of isopropanol.

When the two reagents have completely dissolved the solutions are mixed under agitation and the solution obtained is left under agitation for 30 minutes.

A gum-like solid then precipitates on adding 200 ml of diisopropyl ether and is dried under vacuum at 70° C. for 3 hours.

The dry residue obtained is ground and purified by washing with ethyl ether (for 6 hours).

The product is filtered off and the residual solvent evaporated to obtain 10 g of product with a yield of 82%. M.P. 118°–120° C.

| Elementary analysis: | Calculated | Found |
|---|---|---|
| C | 60.34 | 60.13 |
| H | 8.01 | 7.99 |
| N | 7.82 | 7.87 |

EXAMPLE 4

Preparation of salt (I) where $R =$

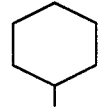

and $X^- =$ tartaric acid anion 10.5 g (0.031 moles) of the derivative (III) in which $R =$

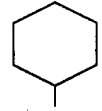

are dissolved in a mixture of 20 ml of isopropanol and 50 ml of diisopropyl ether, and 4.58 g (0.03 moles) of L-tartaric acid are dissolved in 50 ml of isopropanol.

When the two reagents have completely dissolved the solutions are mixed under agitation and the solution obtained is left under agitation for 30 minutes.

A gum-like solid then precipitates on adding 200 ml of diisopropyl ether and is dried under vacuum at 80° C. for 3 hours.

The dry residue obtained is ground and purified by washing with ethyl ether (for about 10 hours).

The product is filtered off and the residual solvent evaporated to obtain 9 g of product with a yield of 60%. M.P. 150°–151° C.

| Elementary analysis: | Calculated | Found |
|---|---|---|
| C | 58.42 | 58.35 |
| H | 7.10 | 7.08 |
| N | 8.52 | 8.49 |

EXAMPLE 5

Preparation of salt (I) where $R=C_7H_{15}$ and $X^-=$ maleic acid anion 1 g (0.0028 moles) of the drivative (III) in which $R=C_7H_{15}$ is dissolved in 20 ml of ethyl ether, and 0.323 g (0.0028 moles) of maleic acid are dissolved in 10 ml of ethyl ether.

The two solutions are mixed and immediately a gum-like product separates and, after decantation, is dried at 70° C. or 2 hours. 1 g of product is obtained with a yield of 85.5%.

| NMR spectrum: | in CDCl$_3$: | 0.90 (t); 1.35 (s); 1.6 (s); 2.45 (m); 2.8 (s); 3.1 (s); 3.25 (d); 3.35–3.7 (m); 5.00 (s); 5.3–5.6 (m); 6.25 (d); 6.45 (s); 6.55 (s); 6.85 (s); 6.9 (dd); 12.5 (s). |
|---|---|---|

| Elementary analysis: | Calculated | Found |
|---|---|---|
| C | 63.16 | 63.02 |
| H | 7.79 | 7.73 |
| N | 8.84 | 8.75 |

EXAMPLE 6

Preparation of salt (I) where $R=C_7H_{15}$ and $X^-=$ citric acid anion 1 g (0.0028 moles) of the derivative (III) in which $R=C_7H_{15}$ is dissolved in 20 ml of ethyl ether, and 0.588 g (0.0028 moles) of citric acid monohydrate are dissolved in 10 ml of ethyl ether.

The two solutions are mixed and immediately the product separates and, after decantation, is dried at 70° C. or 2 hours. 1.2 g of product are obtained with a yield of 75%.

| Elementary analysis: | Calculated | Found |
|---|---|---|
| C | 56.94 | 56.85 |
| H | 7.56 | 7.48 |
| N | 7.38 | 7.31 |

We claim:

1. Organic salts of physostigmine derivatives, having the following general formula:

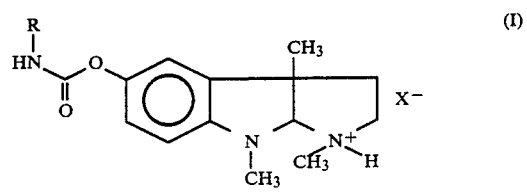

in which R is a linear or branched $C_2$–$C_{12}$ alkyl or a cycloalkyl, and $X^-$ is he anion of an organic acid.

2. Salts as claimed in claim 1, wherein $X^-$ is the anion of an organic acid selected from the group comprising tartaric acid, maleic acid and citric acid.

3. A salt as claimed in claim 1, wherein R is $C_7H_{15}$ and $X^-$ is the anion of tartaric acid.

4. A process for preparing organic salts of physostigmine derivatives, having the following general formula:

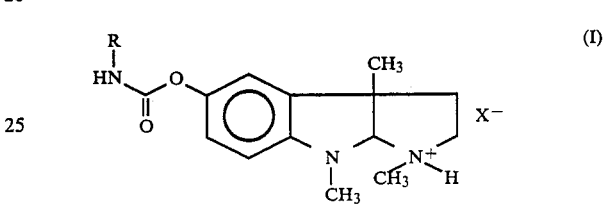

in which R is a linear or branched $C_2$–$C_{12}$ alkyl or a cycloalkyl, and $X^-$ is the anion or an organic acid, said process comprising the following steps:

(a) hydrolyzing physostigmine in absolute ethanol under a nitrogen atmosphere at ambient temperature by treatment with aqueous 5–30% w/w NaOH or KOH solutions, followed by treatment with 1N HCl to obtain eseroline (II)

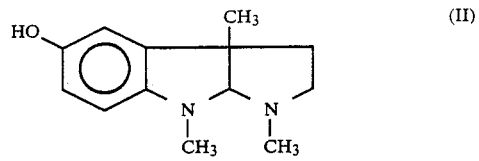

which is purified by crystallization from a 1:1 benzene/petroleum ether mixture;

(b) treating the eseroline, in the presence of traces of Na or solid NaOH under a nitrogen atmosphere at ambient temperature, with an isocyanate of formula R—N=C=O in which R is a linear or branched $C^2$–$C_{12}$ alkyl or a cycloalkyl, by slowly adding a solution of isocyanate in ethyl ether to a solution of eseroline in ethyl ether until the two reagents are in equimolar ratio, to obtain the corresponding physostigmine derivative (III)

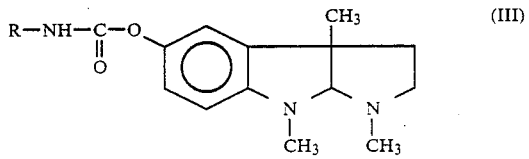

in which R has the aforesaid meaning;

(c) salifying said physostigmine derivative (III) in an organic solvent by mixing at ambient temperature a solution of derivative (III) with a solution of an organic acid to obtain the salt (I).

5. A pharmaceutical composition having acetylcholinesterase inhibition properties, wherein the active ingredient is an effective amount of an organic salt of physostigmine derivatives according to claim 1.

6. The pharmaceutical composition of claim 5, comprising an aqueous solution of the organic salt.

7. The pharmaceutical composition of claim 5, wherein in general formula (I), $X^-$ is the anion of an organic acid selected from the group consisting of tartaric acid, maleic acid and citric acid.

8. The pharmaceutical composition of claim 5, wherein in general formula (I), R is $C_7H_{15}$ and $X^-$ is the anion of tartaric acid.

9. A process as claimed in claim 4, wherein said solution of (III) is a solution in isopropyl ether or in isopropyl alcohol or in mixtures thereof, to the extent of 5–25 ml of solvent per g of (III).

10. A process as claimed in claim 4, wherein said organic acid solution is a solution in isopropyl alcohol to the extent of 5–35 ml of solvent per g of acid.

11. A process as claimed in claim 4, wherein said mixing is carried with equimolar quantities of the two reagents.

* * * * *